United States Patent [19]
Hocherl et al.

[11] Patent Number: 5,549,615
[45] Date of Patent: Aug. 27, 1996

[54] METHOD AND APPARATUS FOR EXTRACTING PACEMAKER ELECTRODES EMBEDDED IN THE HEART

[75] Inventors: Manfred Hocherl, Efringen-Kirchen; Jorg Reinhardt, Grenzach-Wyhlen, both of Germany

[73] Assignee: VascoMed Institut fur Kathetertechnologie GmbH, Weil am Rhein, Germany

[21] Appl. No.: 296,366

[22] Filed: Aug. 25, 1994

Related U.S. Application Data

[63] Continuation of Ser. No. 612,617, Nov. 13, 1990, abandoned, and Ser. No. 952,498, filed as PCT/DE91/00490 Jun. 10, 1991, abandoned.

[30] Foreign Application Priority Data

Nov. 11, 1989 [DE] Germany .......................... 39 37 594.3
Jun. 11, 1990 [DE] Germany .......................... 40 18 681.4

[51] Int. Cl.⁶ ............................................. A61B 17/50
[52] U.S. Cl. ................................ 606/108; 606/1; 607/127
[58] Field of Search ............................ 606/1, 108, 113, 606/127, 138, 157, 198, 129; 128/741, 785, 20, 749, 642; 623/1, 2, 10, 12; 607/125–128

[56] References Cited

U.S. PATENT DOCUMENTS

| | | |
|---|---|---|
| 68,647 | 9/1867 | Palmer . |
| 125,337 | 4/1872 | Schulc . |
| 945,741 | 1/1910 | Birkenkamp . |
| 2,730,101 | 1/1956 | Hoffman . |
| 2,751,912 | 6/1956 | Christoni . |
| 3,754,555 | 8/1973 | Schmitt . |
| 3,831,585 | 8/1974 | Brondy et al. . |
| 3,837,345 | 9/1974 | Matar . |
| 4,136,701 | 1/1979 | Barton et al. . |
| 4,289,144 | 9/1981 | Gilman . |
| 4,345,599 | 8/1982 | McCarrell . |
| 4,471,777 | 9/1984 | McCorkle, Jr. . |
| 4,479,500 | 10/1984 | Smits . |
| 4,574,800 | 3/1986 | Peers-Trevarton . |
| 4,582,056 | 4/1986 | McCorkle, Jr. . |
| 4,763,668 | 8/1988 | Macek et al. . |
| 4,765,332 | 8/1988 | Fischell et al. . |
| 4,913,164 | 4/1990 | Greene et al. . |
| 4,969,458 | 11/1990 | Wiktor . |
| 4,990,151 | 2/1991 | Wallsten . |
| 5,009,659 | 4/1991 | Hamlin et al. . |
| 5,011,482 | 4/1991 | Goode et al. . |
| 5,011,488 | 4/1991 | Ginsburg . |
| 5,019,090 | 5/1991 | Pinchuk . |
| 5,040,544 | 8/1991 | Lessar et al. . |

FOREIGN PATENT DOCUMENTS

| | | |
|---|---|---|
| 03868568 | 5/1990 | European Pat. Off. . |
| 3708133 | 9/1988 | Germany . |

OTHER PUBLICATIONS

Research Diclosure No. 29977, Coil Traction Stylet, By James E. Graf And James L. Jula.

Primary Examiner—Angela D. Sykes
Assistant Examiner—Michael Peffley
Attorney, Agent, or Firm—Baker & Daniels

[57] ABSTRACT

The invention relates to a method and apparatus for extracting a pacemaker electrode whose electrode head has become embedded in the heart. An extractor including an elongated hollow shell, a wire which is located therein and which is movable relative to the shell, and an extractor head attached to the end of the wire. The extractor head includes spreadable barbs, the free ends of which can be spread out radially outwardly to hook into the wall of the lead of the embedded electrode. The extractor head is inserted into a lumen of a pacemaker electrode lead. When the wire is pulled the barbs will hook into the lumen wall. A handle is attached to the other end of the wire for exerting a pulling force on the electrode lead and the electrode when it has become firmly engaged with the umbrella head whereby the electrode will be dislodged from the heart.

10 Claims, 3 Drawing Sheets

METHOD AND APPARATUS FOR EXTRACTING PACEMAKER ELECTRODES EMBEDDED IN THE HEART

CROSS REFERENCE TO RELATED APPLICATIONS

This is a continuation of U.S. patent application Ser. No. 07/612,617 filed Nov. 23, 1990, now abandoned, and entitled "Method and Apparatus for Extracting Ingrown Electrode Spirals from a Body Organ" and which in turn was based on German Patent Application No. P 39 37 594.3 filed Nov. 11, 1989; and U.S. patent application Ser. No. 07/952,498, filed as PCT/DE91/00490, Jun. 10, 1991, now abandoned, and entitled "Device for Extracting a Pacemaker Helical Electrode Embedded in the Heart" which in turn was based on International Application No. PCT/DE91/00490 having an International filing date of Jun. 10, 1991 and which designated the United States.

BACKGROUND OF THE INVENTION

The invention concerns a method for extracting a pacemaker lead whose electrode head has become embedded in a body organ such as the heart, by means of exerting a traction force on the distal lead end.

A method frequently applied for removing nonfunctioning or infected pacemaker leads and their electrodes from the body is the so-called continuous traction method, whereby the lead with its electrode is exposed in the pacemaker pocket and is stressed for hours and days by a continuous traction force of a magnitude between 100 and 500 grams, until the electrode separates from the body organ tissue. A weight acts as traction load on the electrode by means of a cable.

The disadvantage of this method is that the continuous traction method often needs to be applied for days, so that the patient is required to remain in bed, connected to the traction device.

Another known method for extracting nonfunctioning or infected embedded pacemaker leads and their electrodes is by the use of a loop catheter, whereby a loop is advanced over the lead up to the electrode embedment site and is then attached to the electrode. Traction can then be applied directly to the electrode at the embedment site.

A disadvantage of the prior art loop method is that a loop catheter should not be used in the case of infected pacemaker electrodes because germs may be carried into the heart as the loop catheter is advanced over the electrode. The use of the continuous traction method greatly affects the emotional and physical condition of the patient because of the enforced long bedrest.

SUMMARY OF THE INVENTION

The problem underlying the instant invention is to facilitate the extraction of implanted, nonfunctional or infected helical leads with their respective electrodes embedded in a body organ. The traction force required to extract the electrode is exerted directly at the embedment site, and infection of the organ by germ migration, such as may be caused by advancing the extraction device over the electrode lead as in the above mentioned loop method, is precluded.

The extraction procedure according to the present invention provides a solution to this problem by the introduction of a thin extractor into the lumen of the helical lead up to the vicinity of the pacemaker electrode head, by the subsequent, tractionally secure connection of the extractor head to the wall of the helical lead, and the application of an individually exertable traction on the helical lead and its electrode until the electrode separates from its embedment site in the body organ.

A novel aspect of the invention is that the extractor head is connected to the wall of the helical electrode lead by expansion of the extractor head to a diameter larger than that of the diameter of the lumen of the helical lead or coil. Modifications of the procedure may additionally consist in establishing the connection of the extractor head to the wall of the helical electrode lead by hooking or positively anchoring the extractor head into the lumen wall or by expanding the extractor head to a diameter which is larger than the lumen diameter and thereafter hooking or positively anchoring the extractor head into the lumen wall of the lead or coil.

A further embodiment of the inventive method provides for considerably improved handling and more accurately locating the connection of the extractor head to the helical electrode lead wall since the attachment of the extractor head into the helical electrode lead wall is effected by relative displacement of a wire which is disposed inside an extractor shell.

To prevent injuries to the body organ, or heart, in the case of overly embedded pacemaker leads or electrodes, and to enable the abortion of the extraction procedure at any time, another embodiment of the inventive method provides the option of releasing the extractor from the helical lead lumen. The connection between the wire and the extractor head can be severed once a predetermined traction force is exceeded. As a modification of this procedure, the wire may be released from the extractor head by twisting the wire and extractor head relative to each other about the helix axis. Additionally the connection between the extractor head and the wall of the helical electrode lead may be released by relative displacement of the internal wire, in the axial direction of the helix, relative to the extractor shell.

The procedures according to the invention provide considerable relief for the physician while sparing the patient physical and emotional discomfort. The extraction of embedded electrodes according to the invention is also performed with greater safety and simplicity, because unnecessary manipulations are avoided and because the need for expensive equipment is largely eliminated.

As stated hereinabove, electrode heads are occasionally so firmly embedded in the heart that the extraction attempt must be aborted due to the risk of injury. In these cases, in accordance with the invention, the connection between the extractor and the helical electrode lead lumen is released and the extractor is removed. This may in certain cases not be readily managed, if the connection between the internal wire and the extractor head cannot be released.

The Applicant has discovered that by rotating the extractor while it is connected to the wall of the helical electrode lead it is possible to release that extractor by twisting it out of the helical turns and thereby removing it completely from the helical electrode lead. When an internal wire is used, the internal wire is rotated in synchronism with the extractor shell to release the extractor from the helical electrode lead.

The invention also provides a suitable apparatus to practice the inventive process. In one embodiment of the invention an extractor having an expandable, spreadable extractor head is provided which can be introduced into the lumen of the helical electrode lead. The extractor head includes at least two barbs which are spring biased radially outwardly so that, upon reversal of the direction of movement of the extractor, the barbs hook into the lumen wall.

Another embodiment of the invention provides an extractor having an extractor shell. An extractor head is attached to an internal wire which is longitudinally movable within the extractor shell. This embodiment provides an apparatus which can be readily manipulated, since the internal wire allows the precise location and adjustment of the extractor head.

In a first embodiment the extractor head is provided with at least two barbs which are arranged on an umbrella head and which can be spread out by relative displacement of the internal wire with respect to the extractor shell. In a second embodiment the extractor head includes a chamber for accommodating an umbrella head with at least two barbs secured thereto. The barbs can be spread out by the effect of spring bias. The barbs are released and spread out upon relative displacement between the chamber and umbrella head so that the barbs are forced out of the chamber. Lastly, according to a still further embodiment the umbrella head is detachably secured to the end of the interior wire.

Still other variations and refinements of these various embodiments are possible based on one of the basic concepts of the invention, namely an extractor head, which will positively grip or hook into the inside wall of the helical electrode lead, to create a connection therewith so that a discrete traction force may be applied to the electrode lead in the immediate vicinity of the point of embedment of the electrode head in the body organ.

By providing an internal wire in the extractor it is possible to selectively manipulate the extractor apparatus and thereby permit various embodiments of the invention which cause the extractor head to engage the inside wall of the electrode lead lumen in order to apply traction force at the desired point of the electrode lead.

The extraction of an overly embedded electrode in the described way may at times fail due to the fact that the electrode is too firmly embedded in the body tissue. The extractor must then be extracted from the lumen. This can be accomplished according to the invention by rotating the extractor out of the helical turns of the electrode lead. A manually operated device is therefor provided at the tending end of the extractor or the extractor shell, to provide a torque thereto. As a variation thereof, the device may be fashioned in such a way that, in the region of the tending ends of the extractor and the internal wire, means are arranged for establishing a rotationally fixed connection between the extractor and internal wire. An additional option is to connect the tending end of the extractor and/or the internal wire to a motor for application of a torque. For the operation of the extractor apparatus a handle and a grip ring are provided which are respectively connected to the internal wire and the extractor shell. For synchronization of the rotary movement between the extractor shell and the internal wire, an additional provision may be that a rotationally fixed connection can be established between the extractor wire handle and the extractor shell grip ring. Furthermore, it may be suitable to provide the handle with a coupling device for the motor.

BRIEF DESCRIPTION OF THE DRAWINGS

Further characteristics and details of the invention will be explained with the aid of the embodiments illustrated in the following drawings, which respectfully show.

Figure 1:
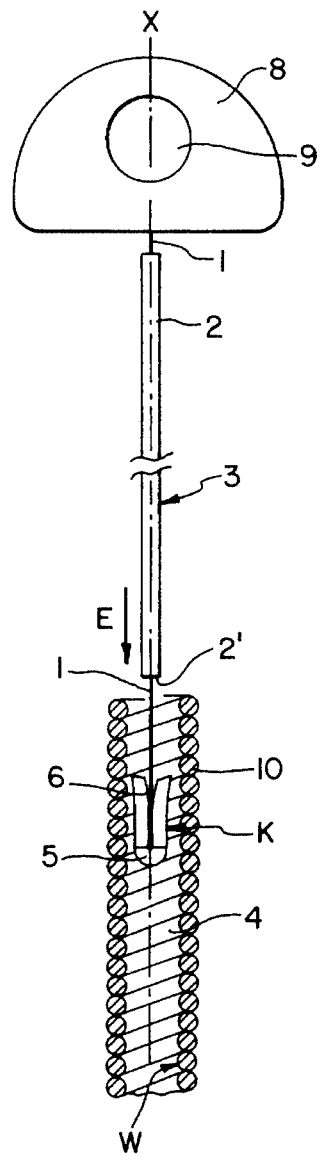
FIGS. 1 shows the apparatus according to the invention, in partial cross-section, in its simplest embodiment as it is introduced in the helical electrode pacemaker lead electrically connected to a pacemaker electrode.

Corresponding reference characters indicate corresponding parts throughout the several views. The exemplifications set out herein illustrate preferred embodiments of the invention, in one form thereof, and such exemplifications are not to be construed as limiting the scope of the invention in any manner.

DETAILED DESCRIPTION OF THE INVENTION

Figure 2:
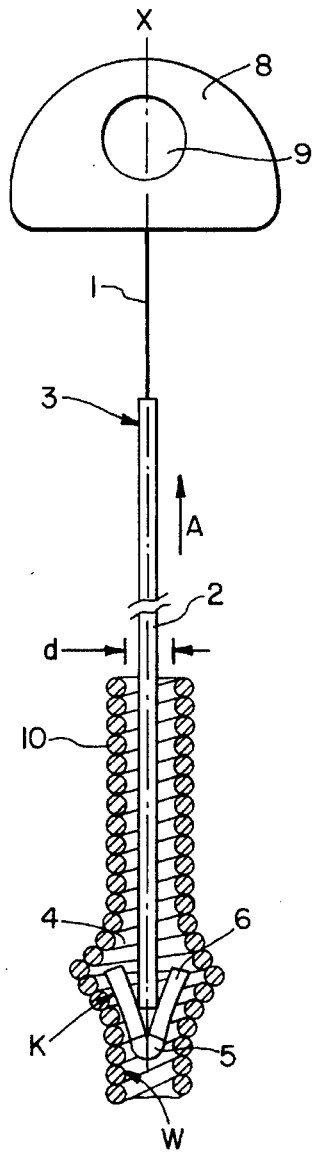
FIG. 2 shows the apparatus according to FIG. 1 hooked into the helical electrode lead.

The embodiment of the extractor according to the invention, illustrated in FIGS. 1 and 2 shows, in a schematic illustration, the front region of the metallic helical electrode lead 10 of a cardiac pacemaker electrode and a component signified as extractor 3, which can be introduced into the lumen 4 of the helical electrode lead 10. While an electrode is commonly provided at the end of helical electrode lead 10 as is well known in the prior art, such an electrode as well as an insulation sleeve around lead 10 have not been shown in the drawings.

Near the bottom end of the extractor 3, as shown in FIG. 1, an extractor head K is attached to a torsionally rigid internal wire 1 which for most of its length extends through an extractor shell 2 of extractor 3. Extractor shell 2 is fashioned as a tube which may be made of a suitable material such as metal or plastic. Two, three or four barbs 6 are provided on extractor head K. Extractor shell 2 has a length of approximately 70 cm and an outside diameter of about 0.4 mm. Wire 1 has a diameter of about 0.2 mm and, with extractor shell 2 retracted, protrudes about 1 cm out of the front end of the extractor shell 2. Extractor head K has a length of about 1.5 mm and consists of a thin section of tube which, starting from its rear end, is slit along a central plane. By slightly spreading the slit ends of the metal tube, spreading tongues or barbs 6 are formed. The free ends of barbs 6 protrude radially outwardly relative to the central axis of the umbrella shaped extractor head K. Upon insertion of the extractor head K into lumen 4 of cardiac pacemaker electrode lead 10, barbs 6 can be spread further in a simple way, namely by exerting a spreading force with the front edge 2' of extractor shell 2 on barbs 6 by relative movement between the internal wire 1 and the extractor shell 2. By sliding the extractor shell 2 forward while holding the wire 1 stationary it is thus possible, by application of a thrust force on shell 2, to anchor the extractor head K into the end of the helical cardiac pacemaker electrode lead 10, so that embedded lead 10 as well as the electrode can be pulled out of the organ tissue of a patient. Anchoring of extractor head K can be accomplished at the desired location within electrode lead 10 by manipulating extractor 3 until head K is located at the desired location, such as near the point of embedment of electrode lead 10 and its electrode (not shown in FIG. 2).

Figure 3:
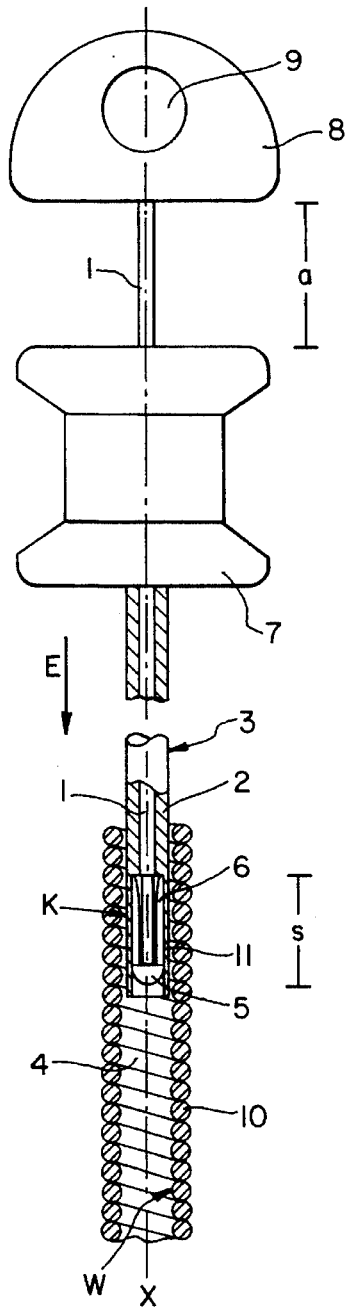
FIG. 3 shows another embodiment of the apparatus, in partial cross-section, with the extractor being introduced into the helical electrode lead.
Figure 4:
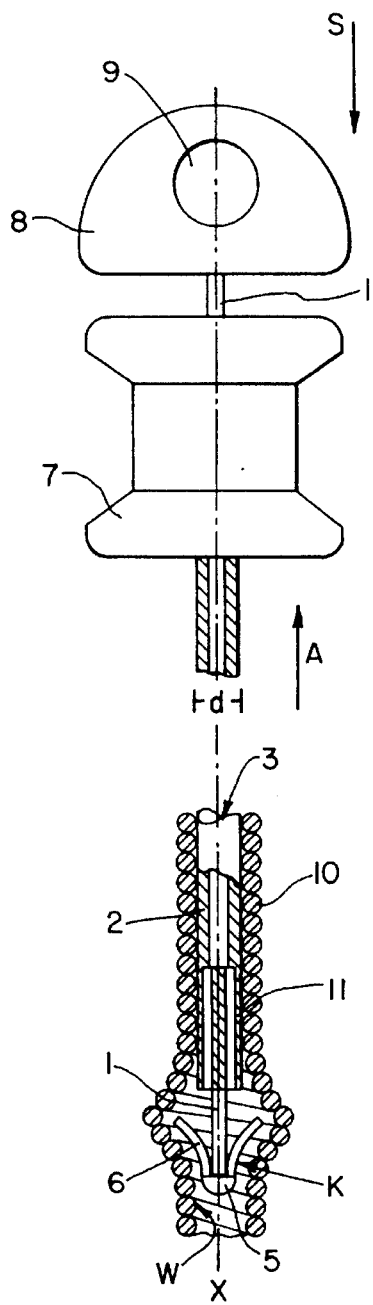
FIG. 4 shows the apparatus according to FIG. 3 hooked into the helical electrode lead.

In another embodiment of the invention as shown in FIGS. 3 and 4 wherein extractor shell 2 extends up to extractor head K, barbs 6 tend to spread outwardly under the effect of a permanently acting spring biasing force. In that embodiment extractor head K and barbs 6 are formed integrally and may be molded from a plastic material. After introduction of umbrella head 5 into helical electrode lead 10 the free ends of barbs 6 contact its wall W. When the extractor head K has reached its final position near the site of embedment of helical electrode lead 10, grip ring 7 and extractor shell 2 which is attached thereto are moved in direction A opposite to the direction of introduction E. Barbs 6 thereupon hook into the lumen wall 4 of helical electrode lead 10 and wedge themselves in place, so that a traction force can be exerted on electrode lead 10. Extractor 3 is provided with a grip ring 7 and a handle 8 which has a grip hole 9 so that extractor 3 can be readily manipulated.

The design also may be such that extractor head K with its umbrella head 5 is detachably connected to extractor 3. The connection is released when a predetermined traction force on umbrella head 5 is exceeded. The value of this predetermined traction force should be such that injuries to the patient at the point of embedment of the electrode in the patient's body are avoided.

In operation extractor 3 is inserted into lumen 4 of helical pacemaker electrode lead 10 in the direction of arrow E. In the embodiment of FIGS. 1 and 2 extractor shell 2 is moved forwardly relative to wire 1 once umbrella head 5 has reached its desired position within lumen 4. The front edge 2' of extractor shell 2 will then cause the free ends of barbs 6 of umbrella head 5 to spread radially outwardly and contact wall W of lumen 4. When handle 8 with wire 1 attached thereto is now pulled in the direction of arrow A as shown in FIG. 2, the free ends of barbs 6 will hook into wall W. Further traction on wire 1 will then tend to loosen pacemaker electrode lead 10 and its electrode from its point of embedment in the organ of the patient. If extractor 3 is so constructed that a predetermined force will disconnect umbrella head 5 from wire 1, a traction force in excess of the predetermined force will sever the connection between wire 1 and umbrella head 5 so that umbrella head 5 is left behind in the electrode lead 10 and no damage to the organ or injury to the patient will occur.

In the embodiment of FIGS. 3 and 4, an umbrella chamber 11 is provided at the end of extractor shell 2. On the front end of wire 1 an umbrella head 5 with barbs 6 attached thereto is provided. A grip ring 7 is attached to the other end of extractor shell 2 whereas wire 1 is attached to handle 8. Movement of grip ring 7 and handle 8 toward each other causes wire 1 to be shifted relative to extractor shell 2 so that umbrella head 5 and barbs 6 slide out of umbrella chamber 1, thus allowing barbs 6 to unfold radially outwardly in umbrella fashion to contact lumen wall W. By reversing the movement between wire 1 and the extractor shell 2, the free ends of barbs 6 will meet resistance and hook into walls of lumen 4, thus establishing a positive connection between extractor 3 and electrode 10 and making it possible to pull electrode lead 10 as well as the electrode head at its end out of the organ by means of handle 8.

Figure 5:
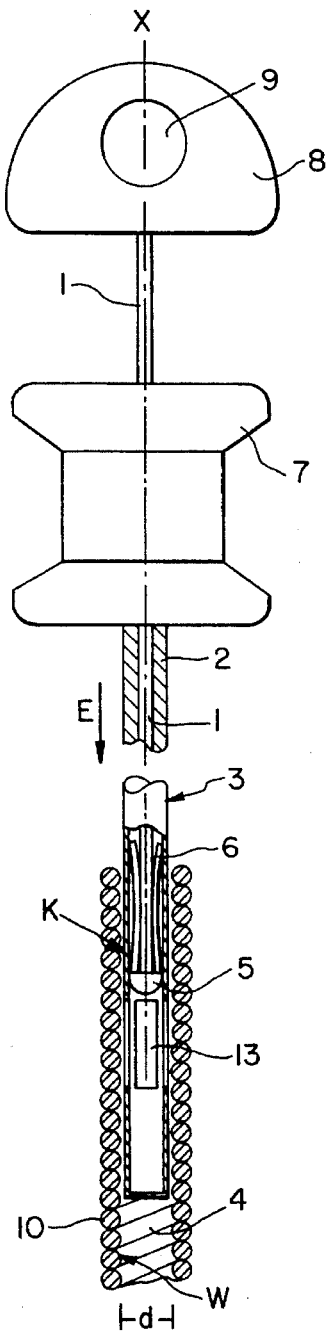
FIG. 5 shows still another embodiment of the apparatus, in partial cross-section, as it is introduced into the helical electrode lead.
Figure 6:
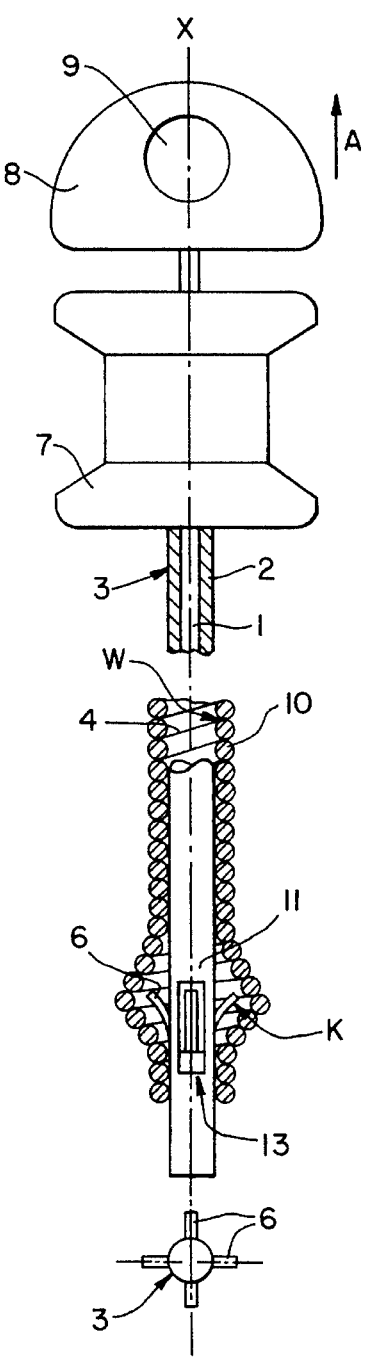
FIG. 6 shows the apparatus according to FIG. 5 hooked in the helical electrode lead.

A further modification is illustrated in FIGS. 5 and 6. The radial wall of umbrella chamber 11 is provided with slots 13 which are aligned with each of barbs 6. Barbs 6 are spring biased radially outwardly. The arrangement and design of slots 13 is such that, once the umbrella head 5 has reached its farthest forwardly advanced position in umbrella chamber 11 and wire 1 is subsequently moved backwardly relative to extractor shell 2, the free ends of barbs 6 will extend outwardly through slots 13 and contact wall W of lumen 4. Similarly to the operation shown in FIGS. 3 and 4, due to the contact of the free ends of barbs 6 with wall W, wall W is deformed and the free ends of barbs 6 will hook into helical electrode lead 10 as wire 1 is pulled by the operator.

The retraction of extended barbs 6 can be brought about by relative displacement of wire 1 relative to extractor shell 2 in the opposite or backward direction as compared with the direction of pull, i.e., in the direction E as shown in FIG. 1. Such retraction of barbs 6 will cause them to be unhooked and released from contact with wall W. Extractor 3 may then be pulled out of lumen 4 and removed by pulling on the grip ring 7. Alternatively, the connection between wire 1 and umbrella head 5 maybe so constructed that head 5 will release from wire 1 upon exceeding a predetermined traction limit.

While not illustrated in the drawings, handle 8 may be provided with a device such as a holding knob or groove, by means of which a rotationally fixed connection can be established between internal wire 1, grip ring 7, extractor 3, and handle 8. By using a suitable coupling, a motor can be connected to handle 8 in such a way that rotational torque will be transmitted to extractor 3 and wire 1. This makes it possible to withdraw extractor 3 and extractor head K from helical electrode lead 10 by rotation of extractor 3 about its longitudinal axis in screw fashion. A preferred embodiment of such an arrangement is illustrated in FIGS. 7, 8 and 9.

Figure 7:
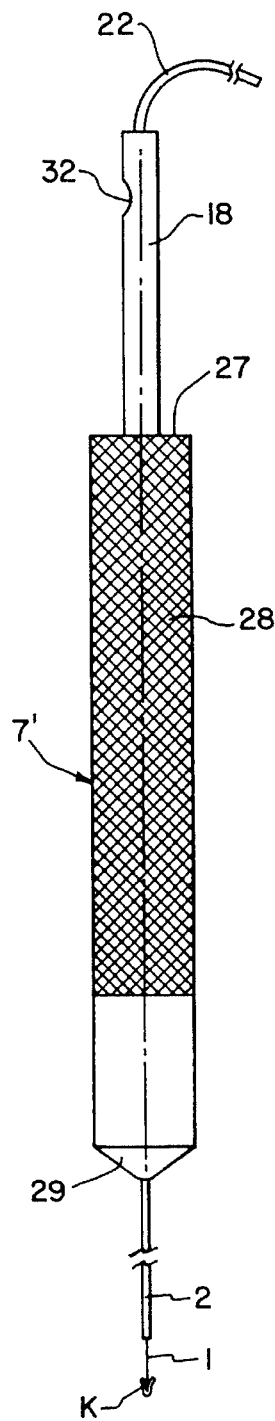
FIG. 7 shows a simplified illustration of an embodiment of the apparatus as used with a motor drive for rotation and removal of the extractor.

As shown in FIG. 7 the outside diameter of extractor head K is smaller than the diameter of lumen 4 of a helical cardiac pacemaker electrode head lead 10. Extractor head K is attached to the front end of internal wire 1 which extends through extractor shell 2, and which, as compared to its actual length, is illustrated greatly shortened in FIGS. 7–9. As can be seen from FIGS. 7 and 8, extractor shell 2, which is fashioned as a thin tube, is provided with a grip 7'. Grip 7' consists of a sleeve 27 which is about 5 cm long and which includes knurls 28. Sleeve 27 is closed at its front end by closure 29. Closure 29 includes an axial bore in which extractor shell 2 is fastened and through which wire 1 extends. Wire 1 extends to connector 18 which is rotatable and axially movable inside sleeve 27. Wire 1 is joined to connector 18 by a weld 30 (FIG. 8). Located at the rear end of connector 18, as shown in FIG. 8, is a weld 31 for connecting pull wire 22 which serves to transmit traction force to connector 18, and thus via wire 1 to extractor head K.

Figure 8:
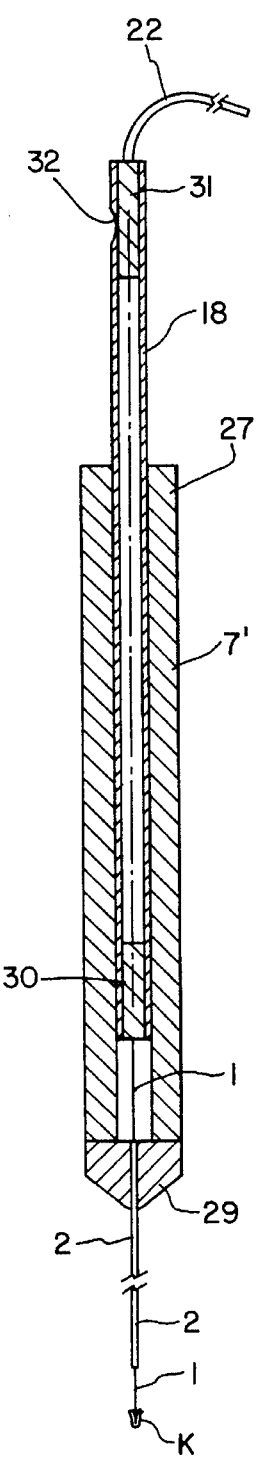
FIG. 8 shows a longitudinal cross-section of the apparatus of FIG. 7.
Figure 9:
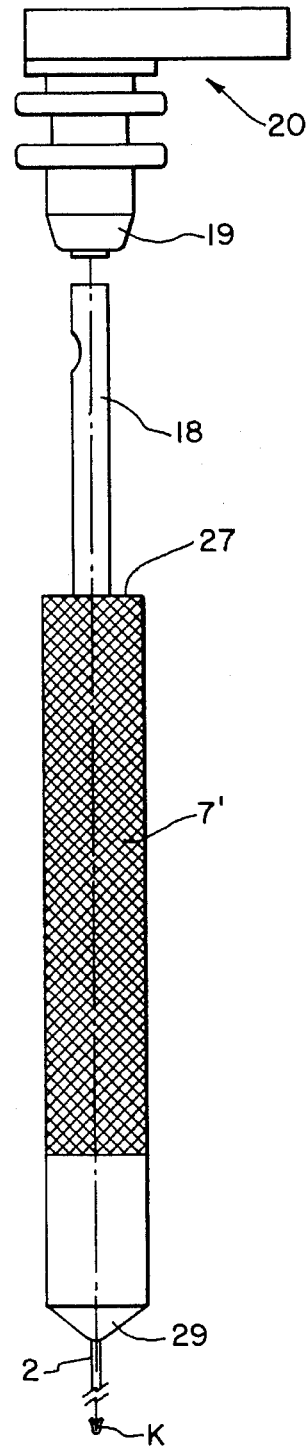
FIG. 9 shows the apparatus according to FIG. 7 together with a motor drive.

On the upper end of connector 18 a recess 32 is provided as shown in FIGS. 7, 8 and 9. Recess 32 allows a fixed coupling of connector 18 with chuck 19 of a drive motor 20 (FIG. 9).

When the extraction device 3 illustrated in FIGS. 1, 2, 7, 8 and 9, is inserted into a lumen 4, extractor head K is first advanced into the immediate vicinity of the front end of electrode lead 10. Once the extractor head K is located at the desired location, grip 7' is advanced while connector 18 is held back. This relative movement of grip 7' and connector 18 causes a spreading force to be exerted by way of extractor shell 2 on extractor head K, thereby causing the free ends of barbs 6 to engage with and hook into wall W of helical electrode lead 10. Once a good connection between head K and helical electrode lead 10 has been established, electrode lead 10 and the electrode may be released from the organ by pulling on connector 18. The traction force may also be applied via pull wire 22, which has a length of about 1 m and is fashioned as a sturdy metal strand with a plastic coating.

If removal of the pacemaker electrode lead 10 and the electrode from the patient's body fails, pull wire 22 is cut off at the upper end of connector 18 and the upper end of connector 18 is assembled in chuck 19 of drive motor 20 (FIG. 9). A ball provided in chuck 19 locks into recess 32. The drive motor 20 allows rotation of connector 18 clockwise or counterclockwise, depending on the direction of rotation of the helix of the electrode lead 10. The rotation of the connector 18 is transmitted via wire 1 on extractor head K, so that barbs 6 can be unthreaded from the coils of helical electrode lead 10. Since the number of turns of the helical electrode lead 10 is very large, the speed of rotation of drive motor 20 is selected so that extraction 3 can be rotated out of pacemaker electrode lead 10 in a relatively short time. Thus, in case of a failed extraction attempt to remove an electrode it is possible to easily completely remove the extractor from the body of the patient.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. In combination a pacemaker helical lead with an associated electrode and a means for extracting said lead and electrode from a heart by exerting traction on the lead, said lead comprising a lumen, said lumen defining a wall, said means for extracting comprising an extractor shell, a wire disposed in said extractor shell, and an extractor head connected to said wire, said wire longitudinally moveable relative to said extractor shell, said extractor head comprising an umbrella head having a plurality of barbs, each said barbs having a free end and an end which is secured to said umbrella head, the free ends of said barbs adapted to be spread outwardly by interaction between said extractor shell and said free ends upon longitudinal movement in a first direction of said wire relative to said extractor shell whereby said free ends can engage with and hook into said lumen wall upon reversal of said longitudinal movement of said wire relative to said extractor shell.

2. The apparatus of claim 1 wherein said extractor shell includes a chamber adapted to accommodate said plurality of barbs, said plurality of barbs adapted to be released from said chamber upon relative displacement between said wire and said extractor shell.

3. The apparatus of claim 1 wherein said wire is connected to a handle and said extractor shell is connected to a grip ring.

4. The apparatus of claim 3 wherein said handle includes a gripping hole.

5. The apparatus of claim 4 wherein said extractor includes an end which is adapted to be connected to manually operable means for application and transfer of a torque.

6. The apparatus of claim 5 further comprising means for rotationally, fixedly interconnecting said extractor shell and said wire.

7. The apparatus of claim 6 further comprising a motor connected to said extractor shell and said wire for transmitting a torque thereto.

8. The apparatus of claim 3 wherein said handle and said grip ring are adapted to be rotationally, fixedly connected to each other.

9. The apparatus of claim 7 wherein said motor includes a chuck which is connected to said wire.

10. An apparatus for extracting a pacemaker helical lead and its associated electrode embedded in a heart by exerting traction on the helical electrode lead, the helical electrode lead defining a lumen having a wall, said apparatus comprising an extractor which is insertable into a said lumen, said extractor including an extractor shell, said extractor shell defining an axial direction, a wire disposed in said extractor shell, an extractor head connected to said wire, said wire and extractor head being longitudinally movable relative to said extractor shell, said extractor head comprising an umbrella head having a plurality of barbs, each said barbs comprising a free end and a second end, said second end secured to said umbrella head, said extractor shell including a chamber adapted to accommodate said plurality of barbs, said plurality of barbs adapted to be released from said chamber upon relative movement of said wire in a first direction relative to said extractor shell, said chamber including slots extending in said axial direction, whereby said free ends of said barbs are spread radially outwardly through said slots by displacement of said wire in a first direction relative to said extractor shell, and are retracted inwardly through said slots by relative displacement in an opposite direction between said wire and said extractor shell whereby said free ends of said barbs will engage with and hook into said lumen wall upon being spread radially outwardly and upon said relative movement in a first direction between said wire and said extractor shell.

\* \* \* \* \*